US005855902A

United States Patent [19]
Ristic et al.

[11] Patent Number: 5,855,902
[45] Date of Patent: Jan. 5, 1999

[54] **METHOD OF ADMINISTERING A VACCINE COMPRISING *TRITRICHOMONAS FOETUS* MEMBRANE SURFACE ANTIGENS BETWEEN 45 AND 300 KILOPALTONS**

[75] Inventors: Miodrag Ristic, Urbana, Ill.; Lionel Wanduragala, Roseville, Minn.

[73] Assignee: Protatek International, Inc., St. Paul, Minn.

[21] Appl. No.: 192,807

[22] Filed: Feb. 7, 1994

Related U.S. Application Data

[63] Continuation of Ser. No. 970,121, Nov. 2, 1992, abandoned.
[51] Int. Cl.⁶ ........................ A61K 39/002; C07K 14/44; A23J 3/20
[52] U.S. Cl. .................................... 424/266.1; 424/269.1; 424/278.1; 530/412; 530/414; 530/424
[58] Field of Search .................................... 530/412, 414, 530/427; 424/269.1, 266.1, 278.1

[56] References Cited

U.S. PATENT DOCUMENTS

| | | |
|---|---|---|
| 2,550,914 | 5/1951 | Cunkelman et al. . |
| 3,265,570 | 8/1966 | Michaels . |
| 3,491,105 | 1/1970 | Klink et al. . |
| 3,892,843 | 7/1975 | Muhler et al. . |
| 3,917,650 | 11/1975 | Santilli et al. . |
| 3,923,831 | 12/1975 | Santilli et al. . |
| 3,988,335 | 10/1976 | Santilli et al. . |
| 4,316,859 | 2/1982 | Michel et al. . |
| 4,327,082 | 4/1982 | Armitage . |
| 4,400,510 | 8/1983 | Michel et al. . |
| 4,428,928 | 1/1984 | Muhler et al. . |
| 4,661,602 | 4/1987 | Myers et al. . |
| 4,683,293 | 7/1987 | Craig . |
| 4,732,989 | 3/1988 | Myers et al. . |
| 4,744,989 | 5/1988 | Morein . |
| 4,824,667 | 4/1989 | Kit et al. . |
| 4,888,170 | 12/1989 | Curtiss, III . |
| 4,976,954 | 12/1990 | Kleber et al. . |
| 5,064,640 | 11/1991 | Klebur et al. . |
| 5,171,568 | 12/1992 | Burke et al. . |
| 5,223,253 | 6/1993 | Hall et al. . |

FOREIGN PATENT DOCUMENTS

| | | |
|---|---|---|
| 922319 | 3/1973 | Canada . |
| 2516317 | 4/1977 | Germany . |
| 1123049 | 8/1968 | United Kingdom . |

OTHER PUBLICATIONS

Goodman et al. "The Pharmalogical Basis for Therapeutics" published by MacMillan Publishing Co. (NY) in 1980 see pp. 951–952.
Friedman, Induction of immune response . . . Vaccine 9(2):122–128 Feb. 1991.
Yule et al. Bovine . . . Parasitology Today 5(12):373–379 1989.
Alderete et al. Infection and Immunity 56(3):28–33 1988.
Huang et al. Am. J. Vet. Research 50(7) 1064–68 1989
Darnell et al. Molecular Cell Biology 1986 pp. 156–160.

Plotkin, S.A. et al. (Ed.) "Vaccines", published by W.B. Saunders Company (Philadelphia), see Chapter 29, especially p. 571, 2nd full paragraph, 1988.
W. G. Kvasnicka et al., "Effect of Vaccination with *Tritichomonas foetus* Immunigens on Reproductive Efficiency in *T. foetus*," United States Department of Agricultures Cooperative State Research Information System, Jul. 1, 1986 — Jun. 30, 1989.
R. Mortimer et al., "The Efficacy of a Vaccine for *Tritrichomonas*," 9th Annual Western Conference for Food Animal Disease Research, Moscow Idaho, Apr. 4–6, 1988.
D.E. Burgess, "Clonal and Geographic Distribution of a Surface Antigen of *Tritrichomonas foetus*", *J. Protozool.*, 35, 119–122, (Feb. 1988).
B.L. Clark et al., "Immunization of Bulls Against Trichomonoiasis", *Aus. Vet. J.*, 60, 178–179 (Jun. 1983).
B.L. Clark et al., "Therapeutic Immunization of Bulls with the Membranes and Glycoproteins of *Trichomonas foetus var. brisbane*", *Aus. Vet. J.*, 61, 65–66 (Feb. 1984).
J.G. Feinberg, "A Method for the Bulk Growth of a Parasitic Protozoan", *Nature* (London), 171, 1165–1166 (Jun. 27, 1953).
W.J. Goodger et al., "Epidemiologic and Economic Analyses of an Unusually Long Epizootic of Trichomoniasis in a Large California Dairy Herd", *J. Am. Vet. Med. Assoc.*, 189, 772–776 (Oct. 1, 1986).
M.R. Hall et al., "Characterization of *Tritrichomonas foetus* Antigens, Using Bovine Antiserum", *Am. J. Vet. Res.*, 47, 2546–2553 (Dec. 1986).
J.L. Hodgson et al., "Characterization of *Tritrichomonas foetus* Antigens by Use of Monoclonal Antibodies", *Infect. Immun.*, 58, 3078–3083 (Sep. 1990).
D.H. Hollander et al., "Vitamin $B_{12}$ Requirement for the Growth of *Trichomonas vaginalis* in vitro", *J. Parasit.*, 71, 683–684 (Oct. 1985).
D.H. Hollander et al., "Isolation of a Stable Clone of the Amoeboid Adherent (AA) Variant of *Trichomonas vaginalis*", *J. Parasit.*, 73, 1074–1075 (Oct. 1987).
B.M. Honigberg, "Trichomonads of Veterinary Importance, Trichomonads of Importance in Human Medicine", *In: Parasitic Protozoa*, vol. II; J.P. Kreier, Ed.; Academic Press (1978).

(List continued on next page.)

*Primary Examiner*—Anthony C. Caputa
*Attorney, Agent, or Firm*—Merchant, Gould, Smith, Edell, Welter & Schmidt, P.A.

[57] ABSTRACT

A subunit vaccine for *Tritrichomonas foetus* and method for preparing such vaccine for use in immunizing and treating animals is provided. The method disclosed involves separating out the antigens by centrifuging homogenized *Tritrichomonas foetus* cells, preferably at about 830×g for about 15 minutes, solubilizing the antigen with an nonionic detergent and completing with saponin. Topical administration, such as intravaginal or intrapretutial administration, of such vaccine preparation in conjunction with subcutaneous administration in combination with other adjuvants is effective to eliminate infection.

6 Claims, 3 Drawing Sheets

OTHER PUBLICATIONS

P.B. Kimsey et al., "Bovine Trichomoniasis: Diagnosis and Treatment", *J. Am. Vet. Med. Assoc.,* 177, 616–619 (Oct. 1, 1980).

M.E. Lamm, "Mucosal Responses to Viruses", *In: Mucosal Immunity and Infections at Mucosal Surfaces;* W. Storber et al., Eds.; Oxford University Press, New York, 277–278 (1988).

C.A. Mims, "The Pathogenesis of Infectious Disease", Academic Press, London — New York, (1976).

B. Morein et al., "Iscom, a Novel Structure for Antigenic Presentation of Membrane Proteins from Enveloped Viruses", *Nature,* 308, 457–460 (Mar. 1984).

G. Overnes et al., "Immune Response After Immunization with an Experimental *Toxoplasma gondii* ISCOM vaccine", *Vaccine,* 9, 25–28 (Jan. 1991).

I.M. Parsonson et al., "Early Pathogenesis and Pathology of *Trichomonas foetus* Infection in Virgin Heifers", *J. Comp. Path.,* 86, 59–66 (1976).

A.E. Pierce, "The Demonstration of an Agglutinin to *Trichomonas foetus* in the Vaginal Discharge of Infected Heifers", *J. Comp. Path.,* 57, 84–97 (1947).

D.O. Rae, "Impact of Trichomoniasis on the Cow–Calf Producer's Profitability", *J. Am. Vet. Med. Assoc.,* 194, 771–775 (Mar. 15, 1989).

J.C. Rhyan et al., "Fetal and Placental Lesions in Bovine Abortion Due to *Trichomonas foetus*", *Vet. Pathol.,* 25, 350–355 (1988).

J. Schnackel et al., "*Trichomonas foetsus* — Vaccine Immunogenicity Trial. *Agri–Practice*", 10, 11–14 (Nov/Dec 1989).

D.A. Street et al., "Evaluation of an Enzyme–Linked Immunosorbent Assay for the Detection of Antibody to *Trichomonas vaginalis* in Sera and Vaginal Secretions", *Br. J. Vener. Dis.,* 58, 330–333 (1982).

METHOD OF ADMINISTERING A VACCINE COMPRISING *TRITRICHOMONAS FOETUS* MEMBRANE SURFACE ANTIGENS BETWEEN 45 AND 300 KILOPALTONS

This is a continuation of application Ser. No. 07/970,121, filed Nov. 2, 1992 now abandoned.

FIELD OF THE INVENTION

The invention relates to an improved subunit vaccine preparation and method for manufacturing such improved vaccine preparation for immunizing animals against *Tritrichomonas foetus.* The vaccine preparation is effective to treat animals infected with *T. foetus* and immunize animals against *T. foetus* infection.

BACKGROUND OF THE INVENTION

Trichomoniasis is a venereal disease caused by the protozoan parasite, *Tritrichomonas foetus.* The infection is confined to the lower reproductive tract of the female; i.e., the uterus, cervix and vaginal vestibule. In the male, *T. foetus* is found in the preputial cavity and less commonly in the urethral orifice. Transmission is almost exclusively by coitus.

Trichomoniasis is a worldwide disease of cattle. In infected cows, clinical manifestations of the disease are: early embryonic death, abortion, pyometra, and infertility, all of which result in reduced calf production. Prevalence increases with the age of the bull, possibly due to deepening of crypts in the preputial epithelium. Therefore, older bulls tend to remain long-term carriers. Infection rates are similar in both *Bos taurus* and *Bos indicus* cattle [Yule et al., *Parasitol. Today,* 5(12), 373–377 (1989)]. A suggestion that there is a breed difference is susceptibility to *T. foetus* has not been substantiated.

The prevalence of trichomoniasis in bulls within a herd reported from around the world varies from 5.8–38.5% in California and 26.4% in South Africa, to 30.6–50% in Australia [Kimsey et al., *J. Am. Vet. Med. Assoc.,* 177, 616–619 (1980)]. Losses due to reduced milk and calf production in a California dairy were calculated at U.S. $665.00 per infected cow [Goodger et al., *J. Am. Vet. Med. Assoc.,* 189, 772–776 (1986)].

Although trichomoniasis is purely a localized infection, the parasite does come into close contact with epithelial tissue at the site of colonization. The presence of circulating anti-*T. foetus* antibodies has been established by several assay systems. Naturally infected cattle have low circulating antibody levels. Highest titers have been seen in animals experiencing abortion and pyometra. However, serological tests, including agglutination, complement fixation, and gel precipitation, have failed to detect naturally infected cattle. Adequate antibody levels have been induced in cattle by inoculation of live parasites as well as various killed preparations of *T. foetus.* Live parasites generally stimulate production of antibody at higher levels than killed preparations. The circulating antibodies, however, reportedly do not come into contact with the parasite and supposedly play no protective role [B. M. Honigberg, "Trichomonads of Veterinary Importance, Trichomonads of Importance in Human Medicine", in *Parasitic Protozoa, Vol. II, J. P. Kreier, ed.* (1978)].

A number of *T. foetus* vaccines have been described [Yule et al., supra (1989); Clark et al., *Aus. Vet. J.,* 60(6), 178–179 (1983); and Clark et al., *Aus. Vet. J.,* 61(2), 65–66 (1984)]. However, a reliable and highly effective vaccine has not been produced. There is a need for a vaccine preparation that can effectively eliminate *T. foetus* infection from animals and immunize uninfected animals.

SUMMARY OF THE INVENTION

The invention is directed to a vaccine preparation and a method for manufacturing an improved vaccine preparation for use in immunizing animals against mucosal pathogens, such as equine influenza virus, *Streptococcus equi, Campylobacter foetus, Tritrichomonas foetus,* and the like. The vaccine can also be used to effectively treat animals infected with such agents.

A preferred vaccine comprises an effective amount of an immuno-stimulating complex having a subunit fraction of *T. foetus* membrane antigens of molecular weights between 45 kD and 300 kD and a saponin. More particularly, the subunit fraction of *T. foetus* membrane antigens corresponds to a supernate fraction of a *T. foetus* cell suspension that has been centrifuged for at least 10 minutes at least at 40×g. More preferably, the antigens of the *T. foetus* subunit correspond to the antigens contained in the supernate of *T. foetus* cells obtained by centrifugation for at least 10 minutes at about 50×g and/or 830×g. Most preferably, the antigens present in the supernate after centrifugation at 830×g for at least about 15 minutes.

The method of the invention comprises providing an antigen suspension obtained from *T. foetus* organisms, including a physiologic saline solution (or a buffer solution), separating the antigen to be used in the vaccine from cell fragments, including structural cell components, nucleii, and the like, and forming an immuno-stimulating complex of selected antigens with saponin. In a preferred embodiment, providing the antigen suspension includes homogenizing the *Tritrichomonas foetus* cells to release the antigens.

The antigens are separated from the cell fragments by centrifugation, preferably for at least 10 minutes at least at 40×g, more preferably for 15 minutes at 50×g, more preferably for 15 minutes at least at 830×g, and most preferably for 15 minutes at 830×g. The antigens thus separated from the cell fragments form the basis for the subunit vaccine.

A nonionic detergent in sufficient quantity is then added and mixed with the dialyzed supernatant for a period of time effective for solubilizing the antigens, ie. to release from the cell membrane. Preferably, the nonionic detergent is N-octyl-β-D-glucopyranoside (OBDG) or octyl phenol ethylene oxide (NP-40) or the like.

Sufficient quantity of a saponin is then added and mixed with the solubilized antigens for a sufficient length of time to form an immuno-stimulating complex (ISCOM). Excess detergent and saponin are removed by dialysis. The dialysis steps can also be done by means of an ultrafiltration system. The ISCOM is suitable for use in immunization through the subcutaneous route.

The vaccine preparation of the invention can be used for treating and immunizing animals, preferably mammals, and most preferably cattle, against *T. foetus.* Administration of the vaccine preparation can be used topically, such as intravaginally or intrapretutially. Preferably, subcutaneous administration is done in conjunction with topical administration.

For intravaginal/preputial immunization or treatment, preferably an adjuvant, such as retinol palmitate (RP), is added to the ISCOM. For intrapretutial/intravaginal administration of the vaccine preparation, preferably, ISCOM with RP and glycerol is used.

BRIEF DESCRIPTION OF THE DRAWINGS

FIG. 1 shows the results of SDS-PAGE Western immunoblot antigen analysis using rabbit anti-*T. foetus* hyperimmune serum. Lane A, B and C are the SDS-page result of an 830×g membrane lysate preparation, 50×g membrane lysate preparation and whole cell lysate preparation, respectively.

DETAILED DESCRIPTION OF THE INVENTION

A. Protective Immunity and Vaccine Composition

Figure 1:
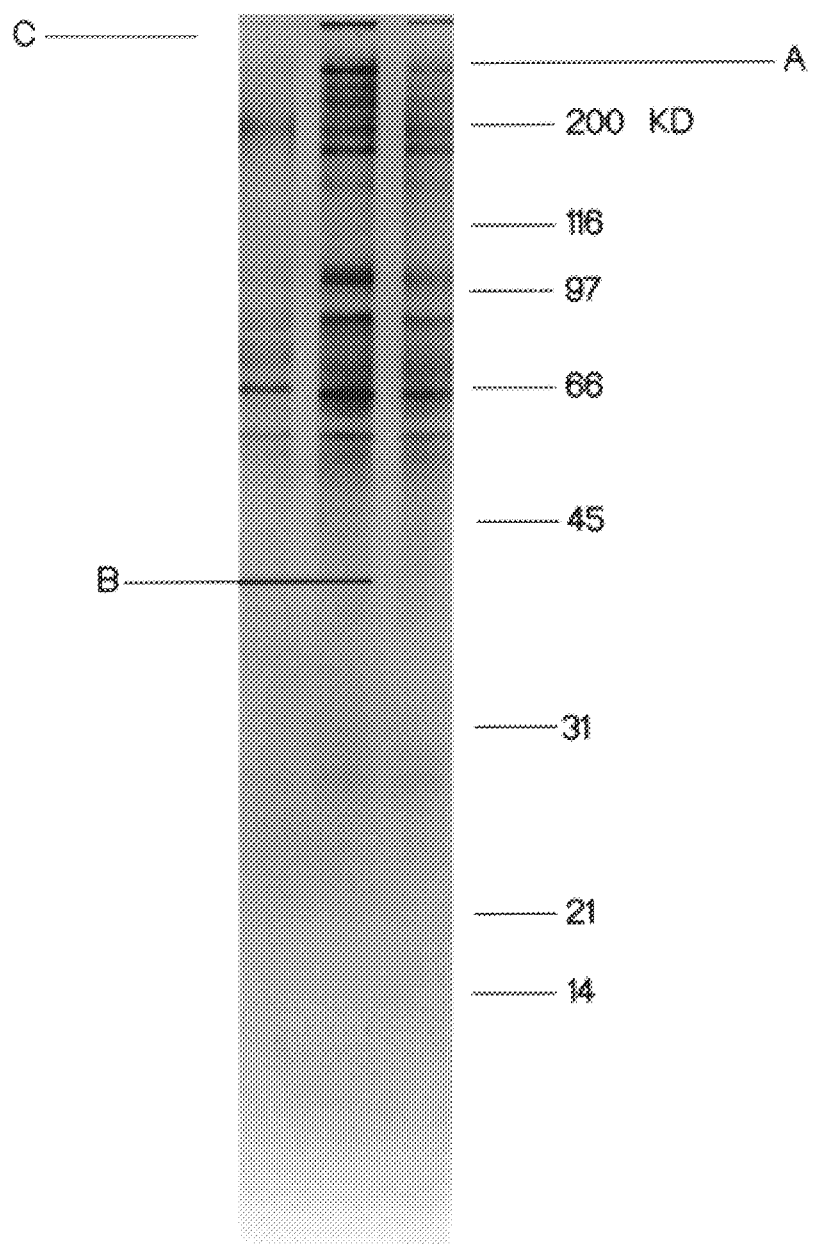

The major host defense mechanism on mucosal surfaces such a those of the vagina, cervix and uterus, which are target sites for *T. foetus*, is provided by antibodies produced locally by plasma cells in the secretory mucosal tissues. Secretory IgA is the principal immunoglobulin on mucosal surfaces and in colostrum. It is a heterodimer of MW of approximately 400 kD consisting of two subunits of the basic four-chain structure with a single J chain, and as the molecule passes across the mucosal epithelium, it acquires an additional "secretory piece".

All natural mucosal infections are known to induce the production of secretory IgA antibodies and there is clear evidence that these antibodies constitute the primary line of defense against these mucosal pathogens [Mims, *The Pathogenesis of Infectious Disease*, Academic Press, London - New York (1976); Lamm, "Mucosal Responses to Viruses" in *Mucosal Immunity and Infections at Mucosal Surfaces*, W. Strober et al., eds., Oxford University Press, New York, pp. 277–278 (1988)]. In natural infection, however, IgA antibody response is slow to develop [Lamm, supra (1988)]. Accordingly, in order to protect the host against a mucosal infection such as *T. foetus*, specific IgA antibodies must be available prior to the onset of the infection. This can only be accomplished by prophylactic immunization designed to stimulate the production of anti-*T. foetus* secretory IgA antibodies. Even though a scientific theory may help to explain the effectiveness of the invention, the adoption of any particular theory is not to be understood as limiting the scope and claims of this invention.

As used herein, the term *Tritrichomonas foetus* refers to the species of parasitic flagellated protozoan that infects the genital tract of animals, particularly cattle. Generally, the organism is characterized by a pear-shaped morphology with multiple flagella in the front, typically three; an undulating membrane; and a trailing flagellum.

The vaccine of the present invention includes a subunit of *T. foetus* to induce the production of anti-*T. foetus* IgA antibodies. As used herein, "subunit" refers to a composition including one or more major membrane surface antigens of *T. foetus*. The immunoactive major surface antigens can be glycoproteins and/or other cell surface components that induce the production of anti-*T. foetus* IgA antibodies. In one preferred embodiment, the vaccine subunit is a membrane surface antigen fraction having a molecular weight between about 45 kD and 300 kD. The subunit is preferably obtained by centrifuging a homogenized cell suspension of *T. foetus* cells for at least 10 minutes at least 40×g to produce the effective antigen fraction.

As described herein, the antigen fraction is separated from the cell debris and employed as the *T. foetus* surface membrane subunit of the vaccine. Preferably, the antigens present in the membrane fractions obtained at about 50×g and/or about 830×g are employed in the vaccine preparation.

The preferred vaccine includes the *T. foetus* subunit fraction, and a saponin. The saponin is exemplified by Quil-A or the like. The amount of saponin employed to create the immuno-stimulating complex will vary from about 0.15 to about 0.20 percent with respect to the amount of antigen to be complexed and will be readily adjusted to effective amounts by one of skill in the art based on the description herein.

The vaccine preparation is administered in a dose of about 0.2 to about 0.3 mg/ml of the immuno-stimulating complex of antigens and saponin. To treat or clear an infected animal of *T. foetus* infection, from about 0.08 to about 0.12 mg/ml of the complex is preferably administered.

Preferably, the vaccine is administered topically, intravaginally, or intrapretutially. We have also found that a combination of topical and parenteral administration is most effective to treat *T. foetus* infection. Similarly, immunization to prevent *T. foetus* infection can be accomplished by topical vaccine delivery alone or, preferably, in combination with parenteral vaccine administration.

One of skill in the art will understand that the antigen/saponin complex (ISCOM) can be combined with other adjuvants, such as an acceptable pharmaceutical carrier such as water, saline, glycerol, retinol palmitate, or the like in amounts that form an effective vaccine composition that can clear up or prevent *T. foetus* infection in animals, preferably female and male bovines. Useful adjuvants include retinol palmitate, sodium fluoride, cholera toxin B, or the like.

We have determined that there unexpectedly appears to be a synergistic protective effect exerted by IgA antibodies in the mucosal secretions and IgG antibodies in animal's serum in response to a vaccine, such as the vaccine described herein. Specifically, the vaccine of the present invention is effective to promote production of anti-*T. foetus* IgA antibodies in amounts sufficient to clear or prevent *T. foetus* infection.

B. Isolates and Culture

Isolates

The two isolates of *Tritrichomonas foetus* used to exemplify this invention were isolates *T. foetus* D1, received from the University of California Davis, and *T. foetus* IDOWY41492 (internal designation), obtained from the Bureau of Animal Health Laboratories in Boise, Id. The antigenic profile of these isolates are representative of *T. foetus*. Analysis of protein and antigen profiles of *T. foetus* from cattle from different geographic locations has shown that no significant difference in composition of total proteins or antigenic proteins was detected and that there are strong antigenic cross-reaction among diverse isolates of *T. foetus* [Huang et al., *Am. J. Vet. Res.*, 50(7), 1064–1068 (1989), incorporated by reference herein]

The first isolate of the organism, designated *T. foetus* D1, originated from a cow with pyometra and had been propagated in vitro at U. C., Davis, before a sample was acquired. The second isolate, *T. foetus* IDOWY41492, was obtained from an infected bull in Owyee County, Id. This isolate was collected from a naturally infected bull, and supplied in 3.0 ml of transport medium in collection pouch. The field sample was propagated in vitro and a stabilate was prepared from the expanded cultures and frozen down for cryopreservation in liquid nitrogen ($LN_2$). Later, a portion of the frozen stabilate was expanded in T-flasks (T-25→T-75) and then scaled up in 1.0-liter bottles from which a master seed stock (MSS), designated #IDOWY41492, was established as follows:

Two 1.0-ml vials of the stabilate prepared from the Idaho isolate of the organism (*T. foetus* IDOWY41492) were used to propagate the organism to a quantity sufficient to prepare a MSS stabilate for cryopreservation. In this regard, the pooled suspension of *T. foetus* was centrifuged at 1500×g for 35 minutes. The pelleted organisms were resuspended in a total of 82 ml of fresh culture medium and a sample was taken to determine their viability and parasite count. Using the standard trypan blue dye exclusion method, the viability and count of this suspension of the parasite was determined to be 93% and $2.69 \times 10^8$ organisms/ml, respectively. A total of approximately five hundred (500) 1.0-ml vials of *T. foetus* stabilate were frozen in *T. foetus* culture medium containing 10% (v/v) dimethylsulfoxide (DMSO). Each vial contained $2.0 \times 10^7$ organisms/ml of parasite suspension.

The antigenic protein profiles of the D1 and IDOWY41492 isolates were typical of *T. foetus*. Researchers have found that there are strong antigenic cross-reaction and noticed no significant differences in the composition of total proteins or antigenic proteins of parasite isolates obtained from cattle in different geographic locations.

*Tritrichomonas foetus* was cultured in *T. foetus* culture medium supplemented with 5% (v/v) donor calf serum (Sigma). Each $LN_2$ stored vial of *T. foetus* stabilate, containing $2.0 \times 10^7$ organisms/ml, was rapidly thawed in a 37° C. water bath, and the contents were aseptically transferred to a T-75 tissue culture flask containing 50 ml of culture medium. The flask was incubated at 37° C. and observed daily for parasite density and fresh medium was added as needed to a maximum of 220 ml per T-75 flask. As soon as the parasite density increased to $5.0 \times 10^6$–$1.0 \times 10^7$/ml, the organisms were transferred to a 40-liter spinner flask to which more medium was added to an initial volume of 2.0 liters. The volume of medium in the spinner flask was gradually increased to 40 liters as the organism increased in number and depleted the nutrients. When the culture reached a parasite density of $8.0 \times 10^6$–$1.0 \times 10^7$/ml, the organisms were harvested for antigen processing.

Three preparations of *T. foetus* were used in characterizing the parasite's antigens by immunochemical analysis using the Western immunoblot technique: (i) whole cell lysate (1.11 mg of protein/ml), (ii) 50×g membrane lysate (1.07 mg of protein/ml) and (iii) 830×g membrane lysate (0.88 mg of protein/ml).

Figure 2:
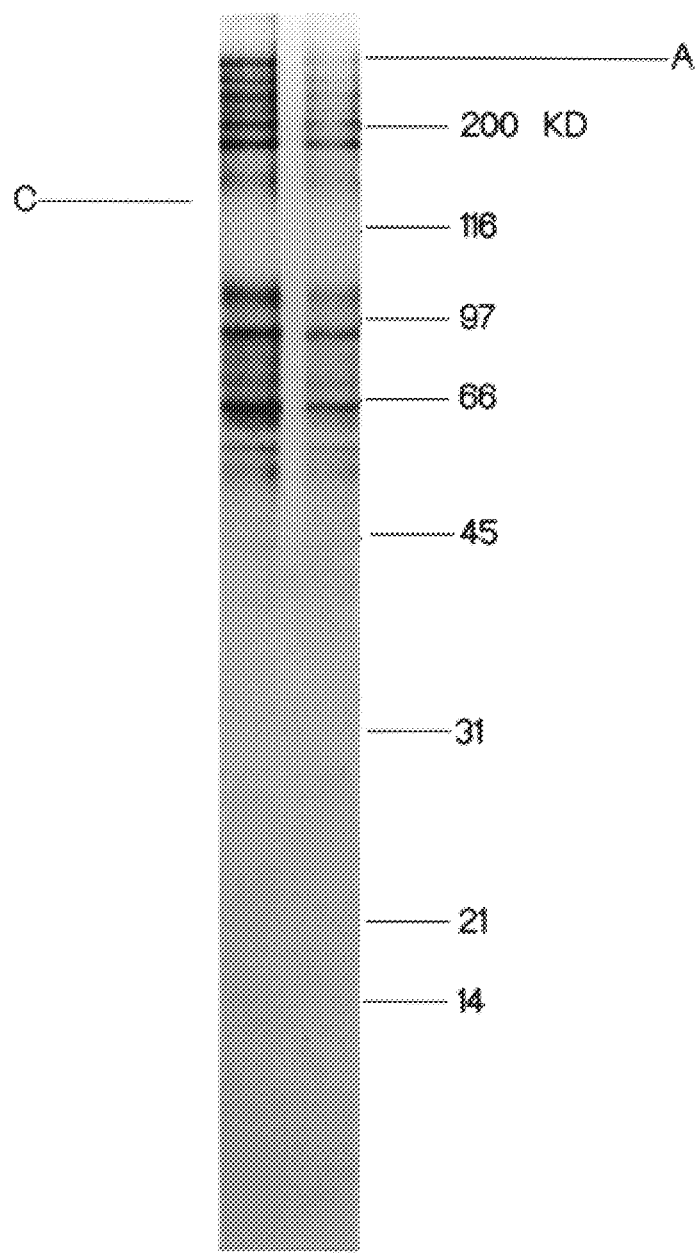
FIG. 2 shows the results of SDS-PAGE Western immunoblot antigen analysis using bovine anti-*T. foetus* hyperimmune serum. Lanes A and B are the SDS-page result of an 830×g and 50×g membrane lysate preparation, respectively.

The antigens detected in the 50×g and the 830×g membrane lysates were similar. A total of 18 antigenic bands were detected on the blots by both the rabbit and bovine immune sera. There were at least 6 high molecular weight polypetides (>200 kD), 1 polypeptide at 180 kD, 5 polypeptides between 55 and 100 kD, 4 polypeptides in the 42–50 kD region, and 2 weak bands in the 28–30 kD region. There were no significant differences in the antigenic makeup of the two isolates (*T. foetus* D1 and *T. foetus* IDOWY41492) used in the development of the vaccine. FIGS. 1 and 2 show the antigen bands of SDS-PAGE Western immunoblot antigen analysis.

Referring to FIG. 1, A is the SDS-PAGE result 830×g membrane lysate preparation, while B and C are the SDS-PAGE result of the 50×g membrane lysate preparation and the whole-cell lysate preparation, respectively. All major antigens present in the whole-cell lysate are apparently retained in the 50×g and 830×g membrane lysates.

Referring to FIG. 2, A and B are the SDS-PAGE result of the 830×g and 50×g membrane lysates, respectively.

C. Immunogen Preparations and Immunizations

The D1 isolate of *T. foetus* was used to produce an exemplary immunogen preparation. It will be appreciated by those skilled in the art that other *T. foetus* isolates can be employed to prepare effective immunogens based on the disclosure herein.

The parasite suspension was washed three times in phosphate buffered saline (PBS), pH 7.2, using a MINI-TAN (Millipore) tangential flow ultrafiltration system equipped with a 70 kD filter, then centrifuged at 8000×g for 30 minutes and resuspended in PBS containing 0.02% (w/v) sodium azide and 1.0 mM phenyl-methylsulfonyl fluoride (PMSF) as preservatives. This suspension was freeze-thawed once then passed through a MICROFLUIDIZER homogenizer (Microfluidics) twice to homogenize the organisms. To produce the antigen component for use in the described vaccine, the homogenate is centrifuged in a centrifuge such as a Heraeus Christ, cryofuge 8000, or the like. The suspension is centrifuged for at least about 10 minutes, preferably at least about 15 minutes, at least at 40×g, more preferably at least about 50×g. Effective membrane subunit fractions are best obtained from the supernate of a suspension centrifuged at about at least 50×g or 830×g for about 10 minutes, more preferably about 15 minutes. By way of example, the above homogenate was centrifuged at 830×g for 15 minutes, and the resulting supernatant was the "830×g membrane lysate". Similarly, a '50×g membrane lysate' was obtained by centrifuging at 50×g for 15 minutes. The 830×g membrane lysate was again centrifuged at 3400×g for another 15 minutes. The latter supernatant was designated the "3400×g membrane lysate". The cell debris containing pellet from the last centrifugation step was resuspended in PBS and designated the "flagellar fraction", as it consisted predominantly of flagella. Both factions were concentrated by lyophilization (freeze-drying) and subsequently reconstituted to the desired protein concentration with deionized water before use. The third antigen preparation consisted of whole *T. foetus* D1 organisms which were frozen and thawed once and then sonicated. This preparation was designated the "whole-cell lysate".

Each antigen preparation was dialyzed overnight against 10 mM Tris-140 mM sodium chloride (TN) buffer, pH 7.4, at 4° C., following which 136 mM of N-octyl-beta-D-glucopyraanoside (OBDG) was added and the mixture was stirred for 1 hour at room temperature to solubilize the antigen. Saponin (Quil-A brand, Superfos) was then added at a concentration of 1.5 mg/ml and the mixture was stirred for 10 minutes at room temperature. It is to be understood that the amount of saponin to be added will depend on the concentration of antigen in the mixture and can be accordingly adjusted to form the immuno-complex. Excess OBDG and saponin was removed by overnight dialysis against 3 changes of TN buffer. The dialysis can be accomplished by dilution and filtration using an ultrafiltration system for retaining molecules larger than 10 kD. The resulting antigen-saponin complex, referred to as the "Immuno-Stimulating Complex" (ISCOM), was used to immunize animals as described herein, including two heifers via the s.c. route in the Example section A2. For intravaginal immunization, retinol palmitate (RP) (Sigma) was added to the ISCOM at a concentration of 41.66667 mg/ml (i.e., 1.0 g RP in 24 ml of ISCOM, equivalent to 12 doses). The amount of RP employed as a vaccine adjuvant can range from about 10 to about 50 mg/ml and can be further adjusted by one of skill in the art based on this disclosure.

D. Tests and Assays for Measuring Immune Responses

Samples

To demonstrate the effectiveness of the ISCOM of the present invention, blood for serum was collected pre- and post-vaccination, at varying time intervals, by jugular venipuncture and the serum was aliquoted into small volumes for storage at −20° C. until use.

Samples of vaginal mucus secretions were also collected pre- and post-vaccination at varying time intervals and treated in three different ways. The first sample was collected by flushing the vaginal vestibule with a sufficient volume of PBS, pH 7.2. The sample was then passed through a 0.22 mm filter, dialyzed against PBS, pH 7.2, and concentrated by lyophilization. It was then reconstituted to the desired dilution with deionized water before use. The second sample was collected and treated similarly, except that it was concentrated by placing the dialysis bag(s) containing the sample in a tray filled with polyvinylpyrrolidone (PVP) powder and letting the bag(s) sit in the PVP powder for a given period of time until the volume was reduced to the desired level. The third sample was collected with a tampon from which the vaginal mucus was subsequently washed into a volume of PBS, pH 7.2, dialyzed against the same buffer and concentrated by lyophilization. It was then reconstituted to the desired concentration with deionized water before use.

Analysis of Samples by Dot-Enzyme-Linked Immunosorbent Assay (Dot-ELISA)

Whole cell *T. foetus* homogenates were prepared as described before, pooled and standardized to an optimal concentration for Dot-ELISA by checker-board titration of the antigen against *T. foetus*-specific serum IgG and vaginal mucus $IgG_1$ and secretory IgA. Commercially obtained alkaline phosphatase-labelled, heavy chain-specific goat anti-bovine IgG conjugate (Kirkegaard and Perry Laboratories, Inc., Gaithersburg, Md.), and alkaline phosphatase-labelled, heavy and light chain-specific sheep anti-bovine $IgG_1$ and anti-bovine IgA conjugates (Bethel Laboratories, Inc., Montgomery, Tex.) were used. 5-bromo-4-chloro-3-indolyl phosphate/nitroblue tetrazolium (BCIP/NBT) was used as the substrate-chromogen system.

The antigen was passively adsorbed, in spots or dots, to nitrocellulose discs (approximately 5 mm in diameter) in 1.0–2.0 ml volumes and let dry at room temperature for at least an hour. The discs were then blocked with 5% (w/v) nonfat dry milk (Carnation®) in PBS, pH 7.2, for 20 minutes and used in the Dot-ELISA immediately or stored dry for later use.

For use in the enzyme immunoassay, the discs were placed singly in a 24-well microtiter plate and washed in excess PBS, pH 7.2. The PBS was discarded and 500 µl of the test sample (serum or vaginal mucus), appropriately diluted, were added to each well containing an antigen-spotted disc and the plate was incubated on a shaker for 2 hours at room temperature. The discs were then washed three times with PBS containing 0.1% (v/v) Tween-20 (PBS-Tween) for 5 minutes each wash. After washing, the discs were each incubated with 500 µl of the appropriately diluted isotype-specific conjugate for 1 hour with gentle shaking at room temperature. They were again washed on the shaker 2 times in PBS-Tween followed by a final wash in excess PBS for 5 minutes each wash. The substrate BCIP/NBT was then added (500 µl/disc) and an enzyme-substrate reaction was let to proceed to completion (20 minutes) and stopped by washing away the excess substrate with deionized water. Positive reactions were evidenced by the development of a purplish gray color of varying intensities on the antigen dots. A negative reaction was evidenced by lack of color development.

Standard Enzyme-Linked Immunosorbent Assay (ELISA) for Measuring Systemic and Vaginal Antibody Responses to *T. foetus* Immunogens For testing serum and vaginal mucus samples for *T. foetus*-specific antibodies (IgG and, $IgG_1$ and secretory IgA, respectively) by the standard ELISA, Linbro Titertek™ (ICN Flow Laboratories, McLean, Va.) 96-well microtiter plates were antigen coated by incubating the plates overnight at 4° C. with a homogenate of *T. foetus* (200 µl/well), which was pre-diluted 500 times with the antigen coating carbonate-bicarbonate buffer to optimize antigenic protein concentration for the assay. Following overnight incubation of the plates with the antigen, they were washed 3 times with PBS, pH 7.2, containing Tween-20 at a concentration of 0.05% (v/v). The plates were then blocked by adding to each well 200 µl of 2% (v/v) bovine serum albumin (BSA) in PBS, pH 7.2, and incubating at 37° C. for half an hour. These plates were either immediately used in the assay or stored at 4° C. for use later.

For the assay, 200 µl of the appropriately diluted test serum or vaginal mucus were added to each well and the plates were incubated at 37° C. for 2 hours. They were then washed 3 times with PBS-Tween (0.05%). The plates were subsequently incubated at 37° C. for 1 hour with the various previously described conjugates, washed three times, and 200 µl of the substrate is added to each well.

Each test sample was run in replicates of 4, and the corresponding 4 wells in a column were run as "blanks" containing unreacted substrate (i.e., blank wells were antigen-coated but were not exposed to either the test sample or the appropriate conjugate). To correct for "background" readings, the average value of the optical density (O.D.) readings of four blank wells was subtracted from the average value of the four replicate O.D. readings of the test wells. For a test sample to be considered positive in the assay, it had to yield a positive-to-negative O.D. reading ratio (P:N ratio) equal to or greater than 2; the negative reading being the O.D. value generated by the pre-immunization serum or vaginal mucus sample of the same animal (also an average of the O.D. readings of 4 wells similarly corrected for by subtracting "blank well" readings).

Western Immunoblot Method

The antigenic proteins of a preparation were separated by sodium dodecyl sulfate-polyacrylamide gel electrophoresis (SDS-PAGE) under reducing conditions, following which they were electroblotted onto nitrocellulose paper. The blotted antigenic polypeptides were then probed with *T. foetus*-specific serum from a hyperimmunized rabbit, as well as serum from an immunized cow, by Western immunoblot analysis.

EXAMPLE

A. Animal Immunization

1. Immunization of Rabbits

Three antigen preparations: 3400×g membrane lysate, flagellar fraction and whole cell lysate as described in section C above were used. Each of these was vaccine-formulated and used to immunize 1 rabbit as follows:

For the initial injection, the antigen was emulsified in complete Freund's adjuvant at a concentration of 1.0 mg protein/ml (Formulation 1). For subsequent booster injections, the antigen was formulated with incomplete Freund's adjuvant at the same protein concentration (Formulation 2). A total of 0.5 mg of *T. foetus* protein in a 1.0-ml delivery volume (one dose-equivalent) was administered s.c. at several sites in the prescapular dorsal region of the rabbit. The first injection (Formulation 1) was administered on day 0. The second injection (Formulation 2) was administered on day 21. The third and fourth injections (Formulation 2) were administered on days 35 and 42, respectively. The rabbits were bled at regular intervals following immunization and serum collected on day 49 (one week after the fourth injection) was used for: (i) assaying for *T. foetus*-specific antibody by the indirect fluorescent antibody (IFA) test, (ii) use in the antigenic analysis of the organism by the Western immunoblot method, and (iii) use in parasite agglutination and immobilization assays.

The IFA test was conducted on serum samples from each of the three hyperimmunized rabbits using intact *T. foetus* D1 organisms as the IFA test antigen to compare the surface binding properties of the sera.

The anti-*T. foetus* antibodies in sera from the 2 rabbits immunized with the 'whole cell' and 'membrane' lysates, respectively, recognized the entire surface of the parasite. Anti-*T. foetus* antibodies in hyperimmune serum from the rabbit that was immunized with the 'flagellar fraction', on the other hand, did not appear to recognize the flagellum as well as was expected, but demonstrated a weak recognition of the rest of the parasite. This indicates the presence of surface antigens in the membrane lysates.

The rabbit anti-whole cell lysate immune serum caused agglutination of the organism with an agglutination titer of 640 (Table I). Similar results were obtained with the anti-flagellum immune serum. The anti-membrane lysate immune serum did not exhibit significantly different results (agglutination titer of 320). Agglutination was visually scored as being greater or less than 50%. All pre-immunization serum samples used as a pool did not cause agglutination.

The parasite immobilization effect of the rabbit anti-whole cell lysate and anti-flagellum sera was not significantly different between the two antigenic preparations (immobilization titers of 160 and 80, respectively). On the other hand, the anti-membrane lysate immune serum did not seem to have any appreciable immobilization activity as it was not able to cause immobilization at a titer greater than the baseline value of 20. As was the case with agglutination, there was no immobilization activity in all the pre-immunization sera collected from these rabbits.

TABLE I

Results of Agglutination and Immobilization of *T. foetus* D1 In Vitro by Hyperimmune Rabbit Serum.[1]

| Serum Titer[2] | *T. foetus* D1 Antigen | | |
|---|---|---|---|
| | Whole Cell Lysate | Membrane Lysate | Flagellar Fraction |
| 0[3] | — | — | — |
| 20 | A/I | A/I | A/I |
| 40 | A/I | A | A/I |
| 80 | A/I | A | A/I |
| 160 | A/I | A | A |
| 320 | A | A | A |
| 640 | A | — | A |
| 1280 | — | — | — |
| 2560 | — | — | — |

[1]Each rabbit administered four s.c. injections of the respective antigen preparation at 14- to 28-day intervals over a 96-day period.
[2]Reciprocal of the highest serum dilution giving a positive reaction in the agglutination/immobilization assay.
[3]Pre-immunization serum.
A = >50% agglutination observed.
I = 100% immobilization observed.
— = Neither agglutination nor immobilization observed.

Using the various *T. foetus* D1 antigen preparations described previously, it was observed that the agglutinating activity of anti-*T. foetus* whole cell lysate serum from a hyperimmunized rabbit was greatly depleted by the 830×g membrane lysate antigen (Table II). Incubation of this antigen with the rabbit anti-*T. foetus* whole cell lysate hyperimmune serum for 30 minutes at 37° C. resulted in greater than 50% inhibition of the serum's ability to agglutinate viable *T. foetus* organisms in 2 to 5 hours in vitro. This inhibitory activity was observable within 2 hours of incubation and persisted up to 5 hours for both the D1 and IDOWY41492 isolates of the organism. The 50×g membrane lysate antigen produced-similar results, while the whole cell lysate antigen did not appear to have the same effect as it was not able to inhibit agglutination after 3 hours of incubation. Similarly, the 50×g pellet had no antigenic activity at all, as evidenced by the fact that there was agglutination observed within 2 hours of incubation which lasted the entire observation period. Furthermore, this lack of inhibitory capability was comparable to that observed with *T. foetus*-positive serum which was not pre-incubated with any of the antigen preparations known to have inhibitory activity (i.e., ability to absorb *T. foetus*-specific antibodies from the immune serum). The *T. foetus*-negative pre-immunization serum remained negative for the assay. This indicates that the membrane lysate is more effective than the whole cell lysate in binding the antibodies elicited by whole cell lysate immunization.

TABLE II

Results of *T. foetus* Agglutination Inhibition Assay
Using Hyperimmune Rabbit Serum

| T. foetus isolate | Incubation time (Hrs) | Without Antigen | | Whole-cell lysate | | 50 × g Pellet | | 50 × g [1]Supernatant | | 830 × g [2]Supernatant | |
|---|---|---|---|---|---|---|---|---|---|---|---|
| | | Pos. | Neg. | Pos. | Neg. | Pos. | Neg. | Pos. | Neg. | Pos. | Neg. |
| IDOWY41492 | 2 | A | — | a | — | A | — | a | — | a | — |
| IDOWY41492 | 3 | A | — | A | — | A | — | a | — | a | — |
| IDOWY41492 | 4 | A | — | A | — | A | — | a | — | a | — |
| IDOWY41492 | 5 | A | — | A | — | A | — | A/a | — | a | — |
| D1 | 2 | A | — | a | — | A | — | a | — | a | — |
| D1 | 3 | A | — | A | — | A | — | a | — | a | — |
| D1 | 4 | A | — | A | — | A | — | a | — | a | — |
| D1 | 5 | A | — | A | — | A | — | a | — | a | — |

[1,2]Membrane Lysates.
A = >50% agglutination observed.
a = <50% agglutination observed.
— = Agglutination not observed with negative serum.

2. Immunization of Two Yearling Holstein Heifers

Two 9-month old heifers (#3628 and #3798) were immunized with the flagellar fraction and 830×g membrane lysate antigen of the *T. foetus* D1 isolate, respectively. These antigens were prepared as described previously, except that they were processed further as aforementioned in section C.

Each of the heifers was administered, in a 2.0-ml dosage volume, 0.45 mg of antigenic protein s.c. and 1.45 mg of protein intravaginally. They were immunized twice, 3 weeks apart.

The purpose of this experiment was to determine the effect of the two antigen preparations on the production of (i) *T. foetus* D1-specific serum IgG and (ii) *T. foetus* D1-specific vaginal secretory IgA.

Immune vaginal mucus samples collected from the 2 Holstein heifers exhibited a greater than 50% agglutinating activity from day 21 post-primary immunization (p.p.i.) through day 35 post-secondary immunization (56 days p.p.i.). This activity (Table III) was exhibited by the immune vaginal mucus at dilutions ranging from 1:20 21 days p.p.i. to 1:640 24 days post-secondary immunization (45 days p.p.i.). The activity then waned down to 1:160 on day 33 post-secondary immunization (54 days p.p.i.) and was back to the 1:20 level by day 35 post-secondary immunization (56 days p.p.i.). On the other hand, the immobilization activity of these vaginal mucus samples remained extremely low throughout the post-immunization observation period, with an observable immobilization activity of less than 50% at the lowest dilution factor of 5.

TABLE III

Results of Agglutination and Immobilization of *T. foetus* D1
by Vaginal Mucus Of Two Immunized Holstein Heifers[1]

| Dilution Factor | Days Post-Immunization | | | | |
|---|---|---|---|---|---|
| | 0[2] | 21[3] | 45 | 54 | 56 |
| 5 | — | A/i | A/i | A/i | A/i |
| 10 | — | A | A | A | A |
| 20 | — | A | A | A | A |
| 40 | — | a | A | A | a |
| 80 | — | a | A | A | a |
| 160 | — | a | A | A | a |
| 320 | — | — | A | a | — |
| 640 | — | — | A | a | — |

[1]Combined data of two heifers; one immunized with the membrane lysate and the other with the flagellar fraction.
[2]Pre-immunization samples.
[3]Second intravaginal dose administered.
A = >50% agglutination observed.
a = <50% agglutination observed.
I = >50% immobilization observed.
i = <50% immobilization observed.
— = Neither agglutination nor immobilization observed.

Figure 3:
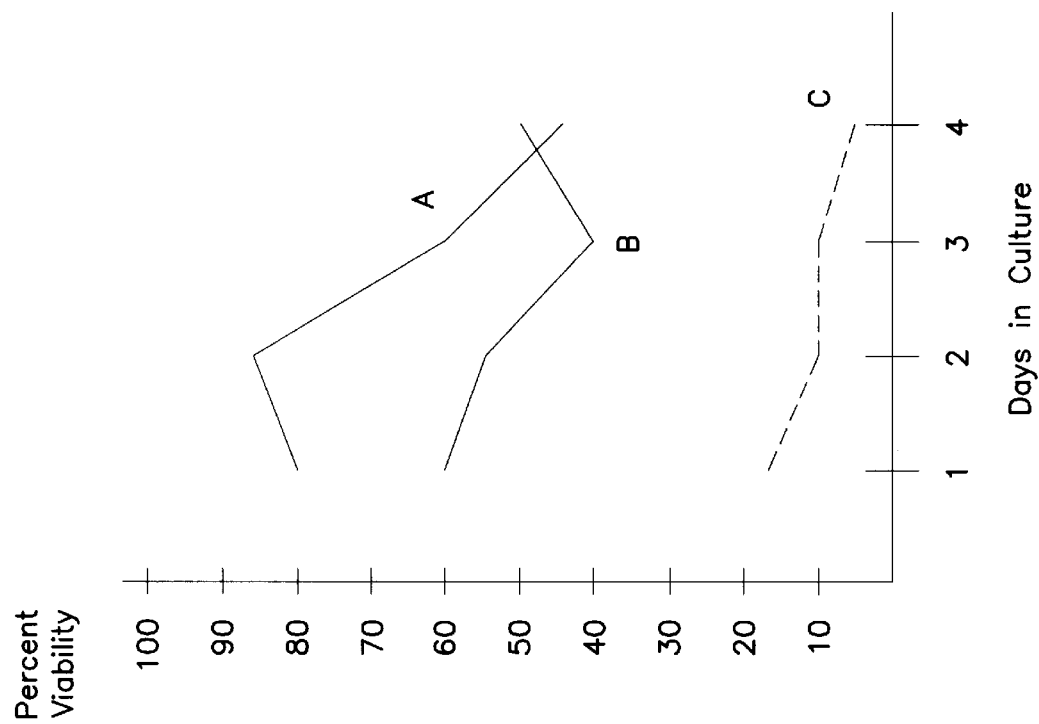
FIG. 3 shows the inhibition of *T. foetus* by vaginal mucus from two immunized heifers: heifer #3628 immunized with flagellar fraction immunogen and heifer #3798 immunized with membrane lysate immunogen.

Referring to FIG. 3, A depicts the effect of pre-vaccination mucus on the growth of *T. foetus* in vitro. B and C depict, respectively, the effect of post-vaccination mucus of heifers #3628 and #3798. The organisms were grown at 37° C. in T-25 tissue culture flask containing 10 ml of culture medium by adding 100 μl of the appropriate vaginal mucus. While incubating, 2.5 ml was removed from the flask and replaced with equal volume of fresh medium daily. Incubation of viable *T. foetus* organisms at 37° C. in the presence of immune vaginal mucus obtained from the 2 Holstein heifers resulted in not less than 95% parasite growth inhibition in vitro, over a 4-day period, by the animal that received the 'membrane lysate' immunogen (animal #3798). The other heifer (#3628) that was immunized with the 'flagellar fraction' exhibited a parasite growth inhibition of approximately 40–60% over a 3-day period, and, by the 4th day of incubation this inhibitory activity had waned, as evidenced by the increase in the number of viable organisms in the culture. The non-immune pre-vaccination vaginal mucus samples were significantly less inhibitory for the growth of the parasite in vitro (15–55% inhibition of growth from day 2 through day 4 in culture), and this relatively steady decline in the viability of the organism was attributed to normal changes in culture conditions over time.

The 2 Holstein heifers immunized with the flagellar fraction and the membrane lysate of *T. foetus* D1 (heifers #3628 and #3798, respectively) were tested for *T. foetus*-specific serum IgG and vaginal mucus secretory IgA at varying time intervals following immunization, using the Dot-ELISA. Both animals responded similarly with respect to *T. foetus*-specific IgG in their sera (Table IV). By day 10 post-secondary immunization (31 days p.p.i.) their serum *T. foetus*-specific IgG levels had risen two to threefold, i.e., from a titer of 320 on day 21 p.p.i. to a titer of 1280 for heifer #3798 and 2560 for heifer #3628 on day 10 post-secondary immunization (31 days p.p.i.). This response remained high through day 33 post-secondary immunization (54 days p.p.i.) when it started to decline. The vaginal mucus *T. foetus*-specific secretory IgA responses of the 2 heifers, on the other hand, were varied. While the heifer that was immunized with the membrane lysate antigen (heifer #3798) became positive for *T. foetus*-specific secretory IgA by day 17 post-secondary immunization (38 days p.p.i.) and remained IgA-positive throughout the rest of the test period (day 35 post-secondary immunization; 56 days p.p.i.), the flagellar faction (heifer #3628) did not appear to be a good *T. foetus*-specific secretory IgA inducer. This heifer did not exhibit the presence of parasite-specific IgA until nearly the end of the test period (day 33 post-secondary immunization or 54 days p.p.i.). Thus the membrane lysate was more effective than the flagellar fraction in inducing secretory IgGA production in the vaginal mucus membrane.

Group 2: was immunized with the ISCOM supplemented with the B subunit of cholera toxin at a concentration of 70 $\mu$g/dose;

Group 3: was immunized with the ISCOM supplemented with sodium fluoride at a concentration of 100 mg/dose.

The quantity of antigenic protein used in this experiment was 0.5 mg of protein/dose for the s.c. route and 1.27 mg of protein/dose for the intravaginal route.

Among the 9 adult Holstein cows immunized with three different *T. foetus* D1 antigen preparations, only the 3 cows in Group 1 (immunized with ISCOM+RP) yielded satisfactory results. By day 25 p.p.i., all 3 animals in this group had turned positive for *T. foetus* D1-specific vaginal secretory IgA (Table V), and this immunoreaction was maintained through the rest of the examination period (i.e., day 30 post-secondary immunization or 55 days p.p.i.). On the other hand, in Group 2 and 3, all but 2 animals (#26, Group 2; and #17, Group 3) remained negative virtually throughout the entire 55-day examination period.

TABLE IV

Results of Dot-ELISA of Sera and Vaginal Mucus for IgA and Secretory IgA, Respectively: Two Heifers Immunized with Differing Fractions[1] of *T. foetus* D1

| | Sample | | | | | | | | | | | | | | |
|---|---|---|---|---|---|---|---|---|---|---|---|---|---|---|---|
| | Serum | | | | | | | | Vaginal Secretions | | | | | | |
| | Days Post-Vaccination | | | | | | | | | | | | | | |
| Animal # | 5 | 12 | 21 | 31 | 38 | 45 | 54 | 56 | 5 | 12 | 21 | 31 | 38 | 45 | 54 | 56 |
| 3628 | – | 80[2] | 320 | 2560 | N/A[3] | 1280 | 1280 | 640 | – | – | ± | ± | ± | ± | + | + |
| 3798 | – | ± | 320 | 1280 | N/A | 1280 | 640 | 320 | – | – | ± | ± | + | + | + | + |

[1]Animal #3628 was immunized with the flagellar fraction and animal #3798 with the membrane lysate.
[2]Titer = reciprocal of the highest serum dilution giving a positive reaction in the Dot-ELISA.
[3]N/A = Sample not available.
+ = *T. foetus* D1-specific IgA detected.
– = *T. foetus* D1-specific IgA not detected.

3. Immunization of 9 Adult Holstein Cows, Effect of Adjuvants

Nine Holstein cows were immunized with *T. foetus* D1 antigen formulated with three different adjuvants for the purpose of comparing the effect of each adjuvant on the cow's vaginal mucosal immune response as measured by the presence of *T. foetus*-specific IgA in vaginal secretions following immunization. Similarly, the effect of the adjuvants on the production of *T. foetus* D1-specific serum IgG was examined. The organisms were washed, homogenized, and further processed as previously described. The subunit fraction was converted into an ISCOM as described before, divided into three equal portions and treated for use in three groups of 3 cows each as follows:

Group 1: was immunized with the ISCOM supplemented with RP as described previously;

TABLE V

Results of Dot-ELISA of Vaginal Mucus for Secretory IgA Following Vaccination of 9 Adult Holstein Cows

| Days Post- | Group 1 | | | Group 2 | | | Group 3 | | |
|---|---|---|---|---|---|---|---|---|---|
| Vaccination | #7 | #13 | #66 | #16 | #26 | #67 | #8 | #17 | #19 |
| *0 | – | – | – | – | – | – | – | – | – |
| 15 | – | ± | – | – | – | – | – | – | – |
| 25 | + | + | + | + | – | – | ± | + | – |
| 40 | + | + | + | – | – | ± | + | + | – |
| 55 | + | + | + | – | + | – | ± | ± | – |

*Day 0 = pre-vaccination samples collected on the day the first intravaginal dose was administered. The second intravaginal dose was administered on day 25 post-primary vaccination.
IMMUNOGENS:
Group 1 - ISCOM + Retinol palmitate
Group 2 - ISCOM + Cholera toxin B
Group 3 - ISCOM + Sodium fluoride
REACTIONS:
+ = *T. foetus* D1-specific IgA detected.
– = *T. foetus* D1-specific IgA not detected.

4. Immunization of 8 Yearling Holstein Heifers, Effect of 2 Different Antigen Preparations Eight yearling Holstein heifers were randomly divided into four groups of 2 animals each. Groups 1 and 2 were immunized with the 50×g membrane fraction, and Groups 3 and 4 with the 830×g fraction. The immunogens (antigens for immunization) were prepared as already described except that OBDG was used at 70 mM, solubilization carried out for 2 hours, and the excess OBDG and saponin were removed by tangential flow ultrafiltration using the Mini-Tan™ (Millipore) system equipped with a 10 kD filter. For each preparation, 0.5 mg of protein/dose were administered s.c. and 1.0 mg of protein/dose was administered intravaginally. Two $T.$ $foetus$ IDOWY41492 antigen preparations and three different preservatives were used. The preparations were: ISCOM+formalin [0.1% (w/v)] and ISCOM+methiolate (1:10 000) for the s.c. route, and ISCOM-RP+formalin [0.1% (w/v)] +methiolate (1:10 000) and ISCOM-RP+methiolate (1:10 000)+glycerol [25% (v/v)] for the intravaginal route). Each dose was delivered in a 2.0-ml volume and each animal received two doses; the first dose administered on day 0 and the second dose on day 22 post-primary immunization. On days 14 and 7 pre-vaccination, serum and vaginal mucus samples were collected from all the animals and verified to be negative for $T.$ $foetus$-specific antibodies.

On day 37 post-secondary immunization, each animal in the four groups of 2 heifers per group was artificially challenged intravaginally with approximately $1.0 \times 10^7$ viable, culture-derived, $T.$ $foetus$ organisms in a 3.0-ml delivery volume, using a 5 c.c. syringe to which an artificial insemination pipette was attached. In addition to the 8 vaccinated heifers, 2 non-vaccinated control heifers were similarly exposed to $1.0 \times 10^7$ viable $T.$ $foetus$ organisms per vaginum. Beginning one week following administration of the challenge dose, vaginal mucus samples were collected weekly for six weeks from all 10 heifers for the isolation of the parasite in vitro.

The 8 Holstein heifers that were immunized, in two groups of 4 animals per group, with two different subunits of the $T.$ $foetus$ IDOWY41492 membrane lysate exhibited identical serological responses when tested against homologous $T.$ $foetus$ antigens by the standard ELISA (Table VI). By day 14 p.p.i., every animal tested had an ELISA titer of at least 640, with the titers ranging from 640 to 2560. These titers increased two- to four-fold by day 12 post-secondary vaccination (34 days p.p.i.), and remained high for both groups (1280–10 240) throughout the remainder of the examination period (i.e., days 35 through 54 p.p.i., or 13 through 33 post-secondary immunization).

TABLE VI

Standard ELISA Results of Serological Responses of 8 Holstein Heifers to Two Subunits of $T.$ $foetus$ IDOWY41492 Membrane Antigen

| Animal | Days Post-Vaccination | | | | | | | |
|---|---|---|---|---|---|---|---|---|
| #[1] | 0[2] | 14 | 22 | 28 | 34 | 42 | 49 | 54 |
| 20 | – | 1280[3] | 1280 | 2560 | 10240 | 5120 | 2560 | 5120 |
| 21 | – | 2560 | 2560 | 5120 | 10240 | 10240 | 5120 | 5120 |
| 22 | – | 640 | 5120 | 5120 | 20480 | 10240 | 10240 | 10240 |
| 23 | – | 1280 | 5120 | 5120 | 10240 | 10240 | 10240 | 5120 |
| 34 | – | 1280 | 640 | 320 | 1280 | 1280 | 640 | 640 |
| 35 | – | N/A[4] | 160 | 1280 | 5120 | 2560 | 2560 | 1280 |
| 38 | – | 640 | 320 | 640 | 2560 | 2560 | 2560 | 1280 |
| 39 | – | N/A | 1280 | 2560 | 5120 | 5120 | 5120 | 2560 |

[1] Animals #20–#23 were immunized with the 50 × g membrane lysate, and animals #34, #35, #38 and #39 were immunized with the 830 × g membrane lysate.
[2] Day 0 = pre-vaccination samples collected on the day the first s.c. dose was administered. The second s.c. dose was administered on day 22 post-primary vaccination.
[3] Titer = reciprocal of the highest serum dilution giving a positive reaction in the standard ELISA;
– = negative.
[4] N/A = Sample not available.

Testing of the 8 heifers by Dot-ELISA, for $T.$ $foetus$-specific secretory IgA in their vaginal mucus following immunization with the respective membrane subunits revealed that by day 14 p.p.i. most of the animals had already started to express parasite-specific IgA in their vaginal secretions (Table VII). This became more evident by day 22 p.p.i., when 3 of the 4 animals that were immunized with the 50×g membrane subunit became conclusively positive, and all 4 animals that received the purer 830×g membrane subunit were similarly positive. this secretory IgA activity for $T.$ $foetus$ IDOWY41492 remained evident through the end of the examination period (day 54 p.p.i. or 32 post-secondary vaccination) for the latter group of animals, while only 2 of the 4 animals in the former group continued to exhibit some activity through the 27th day post-secondary vaccination (day 49 p.p.i.), with the other 2 showing no activity at all by the end of the examination period.

TABLE VII

Results of Dot-ELISA of Vaginal Secretory IgA Responses of 8 Holstein Heifers to Two Subunits of $T.$ $foetus$ IDOWY41492 Membrane Antigen

| Animals #[1] | Days Post-Vaccination | | | | | | | |
|---|---|---|---|---|---|---|---|---|
| | 0[2] | 14 | 22 | 28 | 34 | 42 | 49 | 54 |
| 20 | – | + | + | + | + | + | ± | – |
| 21 | – | – | ± | + | + | + | + | + |
| 22 | – | ± | + | + | + | + | + | ± |
| 23 | – | – | + | + | + | + | ± | – |
| 34 | – | ± | + | + | + | + | + | + |
| 35 | – | + | + | + | + | + | + | ± |
| 38 | – | ± | + | + | + | + | + | + |
| 39 | – | ± | + | + | + | + | + | ± |

[1] Animals #20–#23 were immunized with the 50 × g membrane lysate, and animals #34, #35, #38 and #39 were immunized with the 830 × g membrane lysate.
[2] Day 0 = pre-vaccination samples collected on the day the first intravaginal dose was administered. The second intravaginal dose was administered on day 22 post-primary vaccination.
+ = $T.$ $foetus$ IDOWY41492-specific IgA detected.
– = $T.$ $foetus$ IDOW41492-specific IgA not detected.

Test results of the standard ELISA performed on the vaginal mucus samples collected revealed that all 8 vaccinated animals expressed $T.$ $foetus$-specific IgG, antibody in their vaginal secretions throughout the 54-day examination period, beginning on day 14 p.p.i. (Table VIII). The animals that were immunized with the cruder 50×g membrane subunit showed a stronger IgG, response than those that received the purer 830×g subunit.

TABLE VIII

Standard ELISA Results of Vaginal Mucus IgG$_1$ Responses of 8 Holstein Heifers to Two Subunits of *T. foetus* IDOWY41492 Membrane Antigen

| Animal #[1] | Days Post-Vaccination | | | | | | | |
|---|---|---|---|---|---|---|---|---|
| | 0[2] | 14 | 22 | 28 | 34 | 42 | 49 | 54 |
| 20 | − | + | + | + | + | + | ± | ± |
| 21 | − | + | + | + | + | ± | ± | ± |
| 22 | − | ± | + | + | N/A[3] | + | + | + |
| 23 | − | + | + | + | + | + | + | + |
| 34 | − | + | + | + | ± | ± | ± | ± |
| 35 | − | ± | + | ± | + | ± | + | + |
| 38 | − | + | + | ± | + | ± | ± | ± |
| 39 | − | ± | ± | + | + | + | + | + |

[1]Animals #20–#23 were immunized with the 50 × g membrane lysate, and animals #34, #35, #38 and #39 were immunized with the 830 × g membrane lysate.
[2]Day 0 = pre-vaccination samples collected on the day the first intravaginal dose was administered. The second intravaginal dose was administered on day 22 post-primary vaccination.
[3]N/A = Sample not available.
+ = *T. foetus* IDOWY41492-specific IgG$_1$ detected.
− = *T. foetus* IDOWY41492-specific IgG$_1$ not detected.

Having detected the presence of *T. foetus*-specific secretory IgA and systemic IgG$_1$ in the post-vaccination samples of vaginal mucus collected from the 8 Holstein heifers, the samples were tested for agglutination and immobilization activity. The test results (Table IX) revealed that by day 20 post-secondary vaccination (42 days p.p.i.), all the animals that were immunized with the 830×g membrane subunit were positive for *T. foetus* agglutinating and immobilizing activity, which was at a greater than 50% level and was maintained through the end of the test period (day 32 post-secondary vaccination or 54 p.p.i.). On the other hand, the 50×g membrane subunit group of animals did not show any significant activity over the same post-vaccination period of examination, as all of them exhibited, on average, an agglutination and immobilization activity of less than 50%.

Following artificial intravaginal challenge of the 8 vaccinated heifers and 2 controls with 1.0×10⁷ viable *T. foetus* IDOWY41492 organisms, vaginal mucus samples were collected weekly beginning on day 7 post-challenge (p.c.) and incubated in *T. foetus* culture medium at 37° C. for 48 hours and examined for the presence of the parasite. Sample collection and incubation was done through day 37 p.c., when the examination of the animals was concluded. Results of the 48-hour incubations (Table X) showed that within one week of the challenge, all the animals, vaccinates plus non-vaccinated controls, had become infected with *T. foetus* IDOWY41492. Further weekly attempts to isolate the organism from these animals beyond day 7 p.c. revealed that by day 23 p.c. the infection was completely cleared by the group of heifers that was immunized with the 830×g membrane subunit, while the group that received the 50×g subunit as immunogen did not clear the infection until day 30 p.c. the non-vaccinated controls, on the other hand, remained infected throughout the six weeks of examination (i.e., the organism was isolated from both control heifers on day 37 p.c.).

TABLE X

In vitro *Isolation of *T. foetus* IDOWY41492 Following Intravaginal Challenge of Each of 10 Holstein Heifers with 1.0 × 10⁷ Parasites

| Animal # | Days Post-Challenge | | | | | |
|---|---|---|---|---|---|---|
| | 7 | 11 | 16 | 23 | 30 | 37 |
| 20 | + | + | + | + | − | − |
| 21 | + | + | + | + | − | − |
| 22 | + | + | + | − | − | − |
| 23 | + | + | + | − | − | − |
| 34 | + | + | + | − | − | − |
| 35 | + | + | + | − | − | − |
| 38 | + | + | + | − | − | − |
| 39 | + | + | + | − | − | − |
| **68 | + | + | + | + | + | + |
| **69 | + | + | + | + | + | + |

*48-hour incubation of vaginal mucosal samples.
**Non-vaccinated controls.
+ = Organism isolated in culture.
− = Organism not isolated in culture.

These experiments show that it is possible to induce the production of *T. foetus*-specific systemic and vaginal anti-

TABLE IX

Summary of Results of Agglutination and Immobilization of *T. foetus* IDOWY41492 by Vaginal Mucosal Secretions from 8 Holstein Heifers Post-Vaccination

| Days Post-Vaccination | #20[1] | | #21 | | #22 | | #23 | | #34 | | #35 | | #38 | | #39 | |
|---|---|---|---|---|---|---|---|---|---|---|---|---|---|---|---|---|
| | A | I | A | I | A | I | A | I | A | I | A | I | A | I | A | I |
| 0[2] | − | − | − | − | − | − | − | − | − | − | − | − | − | − | − | − |
| 28 | N/A[3] | N/A | N/A | N/A | − | − | − | − | N/A | N/A | − | − | − | − | N/A | N/A |
| 34 | N/A | N/A | N/A | N/A | ± | ± | ± | ± | N/A | N/A | ± | ± | − | − | N/A | N/A |
| 42 | ± | ± | + | + | + | + | ± | ± | + | + | + | + | + | + | + | + |
| 49 | ± | ± | ± | ± | ± | ± | ± | ± | + | + | + | + | + | + | + | + |
| 54 | + | + | ± | ± | ± | ± | ± | ± | + | + | + | + | + | + | + | + |

[1]Animal I.D. number (n = 8).
[2]Day 0 = pre-vaccination samples collected on the day the first dose was administered intravaginally. The second intravaginal dose was administered on day 22 post-primary vaccination. Animals #20–#23 were immunized with the 50 × g membrane lysate antigen, and animals #34, #35, #38 and #39 with the 830 × g membrane lysate antigen.
[3]N/A = Sample not available.
A+ = >50% agglutination observed.
A− Agglutination not observed.
I+ = >50% immobilization observed.
I− = Immobilization not observed.

bodies which can synergistically act to eliminate the infection. These experiments further indicate that with use of the proper combination of *T. foetus* antigen plus adjuvant(s), and the dual immunization by the parenteral (e.g., s.c.) and intravaginal routes, it is possible to stimulate the production of parasite-specific serum IgG, as well as parasite-specific vaginal mucosal secretory IgA, antibodies which are protective against *T. foetus* infection. Specifically, *T. foetus*-specific secretory IgA appears to work in a synergistic manner with *T. foetus*-specific IgG, and other subclasses of IgG (possibly $IgG_2$) which are found in vaginal mucus of vaccinated animals, presumably as components of the inflammatory transudate. The use of a purified membrane subunit fraction of the organism complexed with Quil-A saponin (ISCOM) and fortified with the immunopotentiating compound, retinol palmitate, appears to be the most effective way to induce solid immunity to infection with *T. foetus*. Attempts to isolate the organism from the heifers that were immunized with the most purified subunit of the parasite's membrane and then artificially challenged with an extremely high dose of *T. foetus*, yielded negative results. The protection of the host against infection with *T. foetus*, therefore, is dependent on the expression of specific IgA antibodies in the lower reproductive tract prior to the onset of the infection. The present invention is the first vaccine of its kind capable of inducing the production of parasite-specific secretory IgA antibody in the absence of an active infection.

5. Immunization of Bulls

Twelve 4-year old Black Angus bulls were randomly divided into 2 groups of 8 vaccinates and 4 non-vaccinated controls. All the bulls were confirmed *T. foetus* culture-positive at 4 and 2 weeks prior to treatment.

The subunit vaccine was prepared as described in section 4. above. Eight of the 12 infected bulls were vaccinated s.c. and treated intrapreputially on days 0 and 29. For s.c. administration, only the ISCOM was used at 0.5 mg of antigenic protein per dose in a 2.0-ml volume, while ISCOM-RP in glycerol was administered intrapreputially at 1.0 mg of antigenic protein in a 5.0-ml delivery volume. Preputial samples for parasite isolation in vitro were collected from 6 vaccinates and 3 controls in transport medium on days 19 and 33 after the administration of the second dose.

Culturing of the preputial samples for the isolation of the organism in vitro revealed that by day 19 post-secondary treatment (day 48 post-primary treatment), when the first sample was collected, all 6 treated bulls had cleared the infection, while the 3 non-treated controls were culture-positive for *T. foetus*. Repeat sampling 14 days after the first collection (day 33 post-secondary treatment) revealed that the 3 control bulls were still harboring the infection, while the 6 bulls that had cleared the infection within 19 days following secondary treatment remained culture-negative for *T. foetus*.

The results of the experiment described above clearly show that the protection conferred by the synergistic effect of local and systemic immune stimulation has caused actual elimination of *T. foetus* from the infected bulls. This finding suggests that a complete resolution of the natural infection was achieved as a direct result of the use of the subunit vaccine as an 'immunotherapeutic.' Until now, chemotherapy has been the only means of treating *T. foetus*-infected bulls, albeit with unpredictable results. The immunotherapy for bovine trichomoniasis using the present invention represents a safer method of controlling *T. foetus* infection, with a potentially longer lasting effect.

The aforementioned experiments clearly demonstrate the effectiveness of the invention in immunization against the infection of *T. foetus*. The invention may be practiced otherwise than as described without departing from its spirit. These experiments are not to be interpreted as limiting the scope and claims of the invention, which are defined by the appended claims:

What is claimed is:

1. A method for treating, *Tritrichomonas foetus* infection, or immunizing to prevent *Tritrichomonas foetus* infection in a male or female bovine, the method comprising:

(a) administering to the male or female bovine an effective amount of an inactivated vaccine composition to treat or to immunize to prevent *Tritrichomonas foetus* infection such that:
      (i) the vaccine composition is administered to a male bovine by an intrapreputial and a parenteral route; or
      (ii) the vaccine composition is administered to a female bovine by an intravaginal and a parenteral route wherein said vaccine composition comprises a saponin and a subunit fraction of *Tritrichomonas foetus* membrane surface antigens of molecular weights between 45 and 300 kD.

2. A method for immunizing to prevent *Tritrichomonas foetus* infection in a male or female bovine, the method comprising:

(a) administering to the male or female bovine an effective amount of an inactivated vaccine composition to prevent *Tritrichomonas foetus* infection such that:
      (i) the vaccine composition is administered to a male bovine by an intrapreputial route; or
      (ii) the vaccine composition is administered to a female bovine by an intravaginal route wherein said vaccine composition comprises a saponin and a subunit fraction of *Tritrichomonas foetus* membrane surface antigens of molecular weights between 45 and 300 kD.

3. The method of claim 1 wherein the parenteral administration is subcutaneous administration.

4. The method of claim 1 wherein the vaccine composition that is administered intravaginally or intrapreputially further comprises retinol palmitate (RP) and glycerol.

5. The method of claim 2 wherein the vaccine composition that is administered intravaginally or intrapreputially further comprises retinol palmitate (RP) and glycerol.

6. The method of claim 3, wherein the subcutaneously administered vaccine composition contains 0.5 mg of membrane surface antigens per dose and the intravaginally or intrapreputially administered vaccine composition contains 1.0 mg of membrane surface antigens per dose.

* * * * *